US007956991B2

(12) United States Patent
Bangalore et al.

(10) Patent No.: US 7,956,991 B2
(45) Date of Patent: Jun. 7, 2011

(54) METHOD AND APPARATUS FOR INTERACTIVE HYPERSPECTRAL IMAGE SUBTRACTION

(75) Inventors: Arjun S. Bangalore, Monroeville, PA (US); David Tuschel, Monroeville, PA (US)

(73) Assignee: ChemImage Corporation, Pittsburgh, PA (US)

(*) Notice: Subject to any disclaimer, the term of this patent is extended or adjusted under 35 U.S.C. 154(b) by 346 days.

(21) Appl. No.: 12/211,960

(22) Filed: Sep. 17, 2008

(65) Prior Publication Data

US 2009/0066947 A1    Mar. 12, 2009

Related U.S. Application Data

(63) Continuation-in-part of application No. 12/000,150, filed on Dec. 10, 2007, now abandoned.

(51) Int. Cl.
*G01N 21/00* (2006.01)
*G01J 3/30* (2006.01)

(52) U.S. Cl. .................... 356/73; 356/317; 356/326

(58) Field of Classification Search ............ 356/73, 356/317, 326, 301; 250/459.1
See application file for complete search history.

(56) References Cited

U.S. PATENT DOCUMENTS

| | | | |
|---|---|---|---|
| 5,194,912 A | 3/1993 | Batchelder et al. | |
| 5,377,003 A | 12/1994 | Lewis et al. | |
| 5,377,004 A | 12/1994 | Owen et al. | |
| 5,394,499 A | 2/1995 | Ono | |
| 5,442,438 A | 8/1995 | Batchelder | |
| 5,493,443 A | 2/1996 | Simon | |
| 5,528,393 A | 6/1996 | Sharp | |
| 5,623,342 A | 4/1997 | Baldwin et al. | |
| 5,689,333 A | 11/1997 | Batchelder et al. | |
| 5,710,626 A | 1/1998 | O'Rourke et al. | |
| 5,862,273 A | 1/1999 | Pelletier | |
| 5,866,430 A | 2/1999 | Grow | |
| 5,901,261 A | 5/1999 | Wach | |
| 5,911,017 A | 6/1999 | Wach | |
| 5,943,122 A | 8/1999 | Holmes | |
| 5,974,211 A | 10/1999 | Slater | |
| 6,002,476 A | 12/1999 | Treado | |
| 6,006,001 A | 12/1999 | Alfano et al. | |
| 6,088,100 A | 7/2000 | Brenan | |
| 6,091,872 A | 7/2000 | Katoot | |

(Continued)

FOREIGN PATENT DOCUMENTS

WO     9511624 A2     4/1995

OTHER PUBLICATIONS

Morris, Hoyt & Treado, "Imaging Spectrometers for Fluorescence and Raman Microscopy: Acousto-Optic and Liquid Crystal Tunable Filter," Applied Spectroscopy, vol. 48, No. 7, 1994.

(Continued)

*Primary Examiner* — L. G. Lauchman
(74) *Attorney, Agent, or Firm* — Duane Morris LLP

(57) ABSTRACT

A method and apparatus of obtaining a spectral image of a plurality of predetermined chemical species. A sample is illuminated to produce photons. These photons are collected to produce a plurality of images for each predetermined chemical species, wherein each image comprises a frame consisting of a plurality of pixels. A wavelength range is identified wherein a chemical species exhibits a unique absorption of radiation. Pixels are identified that do not comprise the chemical species. The steps may be repeated for a plurality of chemical species. If more than one chemical species is present, the contribution of each in a pixel is separated and separate spectral images of each species is composed.

20 Claims, 2 Drawing Sheets

U.S. PATENT DOCUMENTS

| | | | |
|---|---|---|---|
| 6,180,415 B1 | 1/2001 | Schultz et al. | |
| 6,222,970 B1 | 4/2001 | Wach | |
| 6,351,706 B1 | 2/2002 | Morimoto | |
| 6,483,641 B1 | 11/2002 | MacAulay | |
| 6,485,413 B1 | 11/2002 | Boppart et al. | |
| 6,571,117 B1 | 5/2003 | Marbach | |
| 6,690,464 B1 * | 2/2004 | Lewis et al. | 356/326 |
| 6,697,665 B1 | 2/2004 | Rava et al. | |
| 7,317,526 B2 * | 1/2008 | Voigt et al. | 356/301 |
| 7,399,968 B2 * | 7/2008 | Lewis et al. | 250/339.12 |
| 7,554,659 B2 * | 6/2009 | Tuschel et al. | 356/307 |
| 7,609,370 B2 * | 10/2009 | Voigt et al. | 356/73 |
| 7,626,696 B2 * | 12/2009 | Zhang | 356/326 |
| 7,733,484 B1 * | 6/2010 | Gupta et al. | 356/326 |
| 2004/0021861 A1 | 2/2004 | Lewis et al. | |
| 2004/0073120 A1 | 4/2004 | Motz et al. | |
| 2005/0006595 A1 * | 1/2005 | Goodwin et al. | 250/458.1 |

OTHER PUBLICATIONS

Morris, Hoyt, Miller & Treado, "Liquid Crystal Tunable Filter Raman Chemical Imaging," Applied Spectroscopy, vol. 50, No. 6, Jun. 1996.

Skinner, Cooney, Sharma & Angel, "Remote Raman Microimaging Using an AOF and a Spatially Coherent Microfiber Optical Probe," Applied Spectroscopy, vol. 50, No. 8, Jun. 1996.

* cited by examiner

METHOD AND APPARATUS FOR INTERACTIVE HYPERSPECTRAL IMAGE SUBTRACTION

The instant application is a continuation-in-part of application Ser. No. 12/000,150, filed Dec. 10, 2007, which is a continuation application of application Ser. No. 11/097>160, Fled Apr. 4, 2005 and now abandoned. The disclosures of both of these applications are expressly incorporated herein by reference in their entirety.

FIELD OF THE INVENTION

The present disclosure relates to the field of spectroscopic analysis and devices therefor, particularly as applied to the identification of chemical species in a sample.

BACKGROUND OF THE INVENTION

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e., chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

Often the sample under study includes a plurality of species in a mixture. Thus, the chemical image of the sample characterizes the sample as a mixture of species. Each specie can be a pure element, a compound of said element with other elements or a compound. While the chemical image of the sample can identify each of the species by using color or some other indication, it fails to communicate the spectral image of each specie independent the mixture. Thus, there is a need for a method and apparatus to interactively obtain the spectral image for the desired specie from a chemical image of the mixture.

The instant disclosure addresses the needs described above. In one embodiment, the disclosure relates to a method of obtaining a spectral image of each of a plurality of predetermined chemical species in a sample, comprising: (a) illuminating the sample with a first plurality of photons to produce a second plurality of photons; (b) collecting the second plurality of photons and producing a plurality of images of the sample using those photons, wherein each of the images comprises a frame consisting essentially of a plurality of pixels; (c) for each of the predetermined chemical species, identifying at least one wavelength range at which the chemical specie exhibits a unique absorption of radiation; (d) identifying at least one wavelength range at which none of the predetermined chemical species exhibits an absorption of radiation; (e) in each of the image frames, identifying which of the pixels do not contain any of the predetermined chemical species; (f) in each of the image frames, identifying which pixels contain only one of the predetermined chemical species; (g) repeating the previous step for each of the predetermined chemical species; (h) in each of the image frames, identifying which pixels contain more than one of the predetermined chemical species; (i) for each pixel that contains more than one chemical species, separating the contribution of each of chemical species; and (j) composing separate spectral images of each of predetermined chemical species in the sample.

In another embodiment, the instant disclosure relates to an apparatus for obtaining a spectral image of each of a plurality of predetermined chemical species in a sample, comprising: (a) an illumination source for illuminating the sample with a first plurality of photons to form a second plurality of photons; (b) an optical device for receiving and directing the second plurality of photons to an imaging device; (c) an imaging device for forming a plurality of images of the sample, each of the images comprising a frame consisting essentially of a plurality of pixels; and (d) a processor in communication with the imaging device and being adapted to: (i) for each predetermined chemical species, identifying at least one wavelength range at which the chemical specie exhibits a unique absorption of radiation; (ii) identifying at least one wavelength range at which none of the predetermined chemical species exhibits an absorption of radiation; (iii) in each of the image frames, identifying which pixels do not contain any of the predetermined chemical species; (iv) in each of the image frames, identifying which pixels contain only a first predetermined chemical species; (v) repeating this step for each of the predetermined chemical species; (vi) in each of the image frames, identifying which pixels contain more than one of the predetermined chemical species; (vii) for each pixel that contains more than one predetermined chemical species, separating the contribution of each predetermined chemical species; and (viii) composing separate spectral images of each predetermined chemical species in the sample.

It is to be understood that both the foregoing general description and the following detailed description are exemplary and explanatory only and are intended to provide further explanation of the invention as claimed.

DETAILED DESCRIPTION OF PREFERRED EMBODIMENTS

Figure 1:
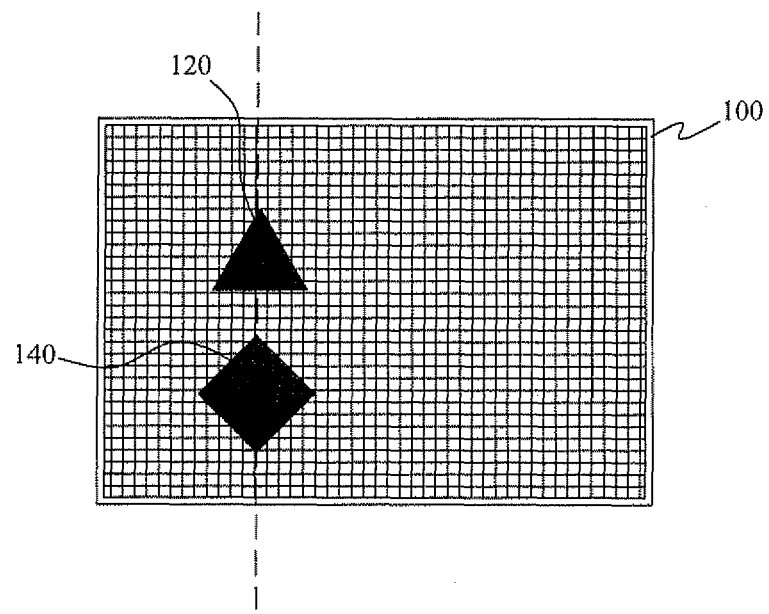
FIG. 1 is a schematic chemical image of a sample having a combination of two species.

A first preferred embodiment of the present invention is directed to methods of obtaining spectral images of predetermined chemical species in a sample. A second embodiment is directed to apparatus for obtaining spectral images of predetermined chemical species in a sample.

The inventive method first requires illuminating a sample with a first plurality of photons to produce a second plurality of photons. The illumination source for use in illuminating the sample may be any suitable source known and available to those skilled in the art. For example, the illumination source may be a quartz tungsten halogen (QTH) lamp source or other broadband while light source, including metal halide lamps, mercury arc lamps or xenon arc lamps. The illumination source may also be a laser or similar device. The illumination source may provide the first plurality of photons directly (e.g. a transmitted light configuration) or indirectly (e.g. a reflected light configuration).

Preferably, the illumination source provides monochromatic light. More preferably, the illumination source provides monochromatic light having a wavelength in the range of 500 nm to 800 nm.

The inventive method further involves collecting the second plurality of photons and producing a plurality of images of the sample using those photons. The second plurality of photons is produced by the sample scattering, emitting, reflecting and/or transmitting photons upon being illuminated by the first plurality of photons.

Collection of the second plurality of photons is preferably accomplished using an optical device. Any suitable optical device known and available to those skilled in the art may be employed in the inventive method and apparatus. Preferably, the optical device includes at least one Filter. Illustrative examples of suitable Filters include, but are not limited to, the following: a tunable filter, a band pass filter, a liquid crystal tunable filter (LCTF), an interferometer, an acousto optical tunable filter (AOTF), a dispersive optical device and a computed tomography imaging spectrometer (CTIS).

According to certain preferred embodiments, the filter is a liquid crystal tunable filter such as a Lyot liquid crystal tunable filter (LCTF), an Evans Split-Element LCTF, an Solc LCTF, a Ferroelectric LCTF, a Fabry Perot interferometer, or a hybrid Filter composed of two or more of thereof.

Once collected, the second plurality of photons is directed to an imaging device for the production of an image of the sample. Illustrative examples of suitable imaging devices include, but are not limited to, focal plane array (FPA) detector, a charge coupled device (CCD) and a complementary metal oxide semiconductor (CMOS) detector. According to certain embodiments, each of the images produced from the second plurality of photons comprises a frame consisting essentially of a plurality of pixels.

The inventive method also requires that at least one wavelength range is identified within which each of the predetermined chemical species exhibits an absorption of radiation. Preferably, each chemical species exhibits an absorption of radiation within a unique wavelength range under the conditions of use. In addition, the inventive method requires identifying at least one wavelength range at which none of the predetermined chemical species exhibits an absorption of radiation. These identification steps may be performed at any point in the performance of the inventive method.

Once the second plurality of photons has been collected and the image(s) produced, pixels that do not contain any of the predetermined chemical species are identified in each image. In addition, pixels that contain only the first of the predetermined chemical species are identified. This step is then repeated for each of the predetermined chemical species, i.e., pixels that contain only a single predetermined chemical species are identified. These identifications are accomplished using the previously determined wavelength range for each chemical species and the previously determined wavelength range for the background (i.e. the wavelength range within which none of the predetermined chemical species exhibits and absorption of radiation).

Once the pixels containing only background or a single chemical species have been identified, the inventive method requires identifying which pixels contain more than one of the predetermined chemical species. Again, such identification is made using the previously determined wavelength range for each chemical species and the previously determined wavelength range for the background. For each of these pixels, the inventive method involves separating the contribution of each of chemical species.

Following the above steps, the inventive method then involves composing separate spectral images of each of predetermined chemical species in the sample. Preferably, these images are hyperspectral images. More preferably, these images are spatially accurate, wavelength resolved hyperspectral images. Using these images, a composite of the sample being examined can be prepared, where each predetermined species and the relative quantity thereof has been identified.

The present invention also include apparatus for performing the inventive methods described above. These apparatus generally include: (a) an illumination source for illuminating a sample with a first plurality of photons to form a second plurality of photons; (b) an optical device for receiving and directing the second plurality of photons to an imaging device; (c) an imaging device for forming a plurality of images of the sample; and (d) a processor in communication with the imaging device.

The processor may be any suitable computing device. Preferably, the processor is adapted to perform the various identifications and separations described above in connection with the inventive method. The processor is also preferably adapted to compose separate spectral images, and more preferably spatially accurate wavelength-resolved hyperspectral images, of each of predetermined chemical species in the sample.

To further illustrate certain embodiments of the present invention in greater detail, reference will now be made to the drawings. FIG. 1 is a schematic chemical image of a sample having a combination of two species. In FIG. 1, frame 100 represents a chemical image at a specific wavelength or Raman shift of a composition having a first species 120 and a second species 140. Frame 100 can be formed by combining several spectra into a chemical image. The specific wavelength or Raman shift frame can be defined by a number of pixels where each pixel is defined by it location (e.g., x, y) and intensity (I). Thus, each pixel in a wavelength or Raman shift frame can be defined as a function of I, x, y. According to one embodiment of the disclosure, frame 100 can be used to interactively subtract out background noise as well as spectral contribution from one or more species to obtain the spectral image of one specie.

Figure 2:
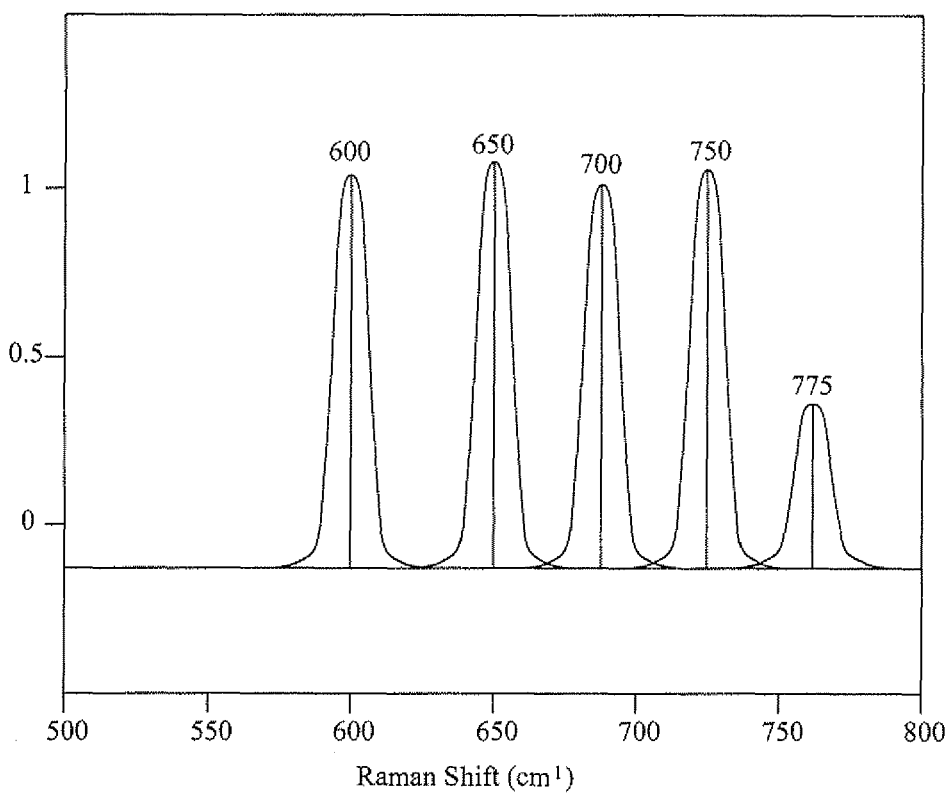
FIG. 2 shows peak Raman intensities and correlated wavelengths for each of the species shown in FIG. 1.

FIG. 2 consists of reference spectra obtained of the pure components known to comprise the sample. Assuming that the composition of each of species 120 and 140 is known, the Raman characteristics for each specie can be obtained. The Raman characteristic can include an expected wavelength for the Raman peak shift for each specie. In FIG. 2, Raman peaks for each of 120 and 140 are combined in one spectrum. Spectrum 200 shows peak Raman wavelengths for species 120 and 140 and their normalized intensity. Specifically, each of peaks 600, 700 and 775 indicate a Raman shift for species 120 and each of peaks 650 and 750 indicate a Raman shift for species 140 of FIG. 1. The characteristic Raman peak for each species identifies its wavelengths/intensity relationship. Based on this information, pixels exhibiting the appropriate wavelength/intensity relationship can be attributed to one of the two species.

After identifying a characteristic Raman peak wavelength for each species, the background wavelength for the frame may be defined. The background wavelength can be caused by intangibles of the optical devices such as signal-to-noise interference, and other common electro-optical losses. The background wavelength can also define a quantifiable intensity uniformly affecting all pixels in the chemical image frame 100. Once the intensity and the wavelength of background noise is identified, all pixels in the Chemical image frame that only relate to the background wavelength can be identified. Thereafter, all pixels defined by wavelength and intensity characteristics similar to that of the known Raman spectra of each specie can be identified.

Once the pixels directed exclusively to the first species or the second species or the background have been identified, the remaining pixels can be attributed to identifying a combination of the first species and the second species, thereby constituting a chemical interface of one or more species. Theses remaining pixels can be said to contain a contribution from each species.

Once the function of each pixel in the frame is defined as one of background, first species, second species or a combination of the first species and second species, a spectral image can be constructed for any one of the species by interactively subtracting contributions from the background and the other species.

In the exemplary embodiment of FIGS. 1 and 2, only two species are present. Thus, by subtracting pixels directed to background and second species, a spectrum for the first species can be constructed and compared to the corresponding reference spectrum. The degree to which the extracted spectrum of the residual image component matches the reference spectrum is a measure of the validity or quality of the interactive hyperspectral image subtraction. To further enhance the first species' spectrum, additional pixels may be included that depict the contribution from both species. To this end, the pixels showing contribution from both species can be normalized to represent the contribution from each species and filtered to remove the contribution from the second species to thereby isolate the first species' contribution to the pixel.

The disclosed method and apparatus enable interactive visualization and comparison of different imaging modes. The interaction is direct and unobstructed. The embodiments disclosed here enable macro-to-micro image exploration as well as specific targeting of regions of interest. In addition, the ability to switch between imaging modes for the same regions allow comparisons that would otherwise not be possible, or alternatively, would be difficult and time consuming. These exemplary steps can be repeated to determine a spectra for the second specie. While the exemplary embodiments of FIGS. 1 and 2 are directed to a sample of only two species, the principles disclosed herein can be extended to a system of sample having multiple species.

Figure 3A:
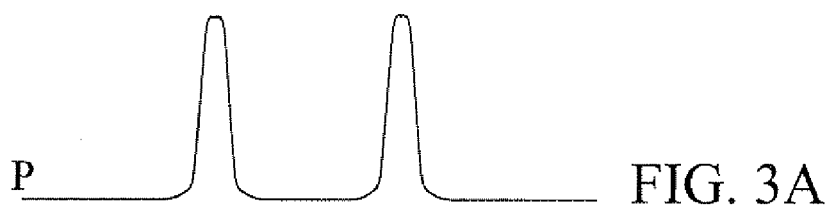
FIGS. 3A-3C illustrate the resulting spectrum from a chemical interaction of two spectra.
Figure 3B:
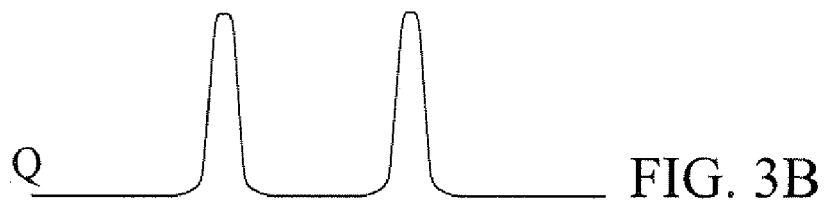
Figure 3C:
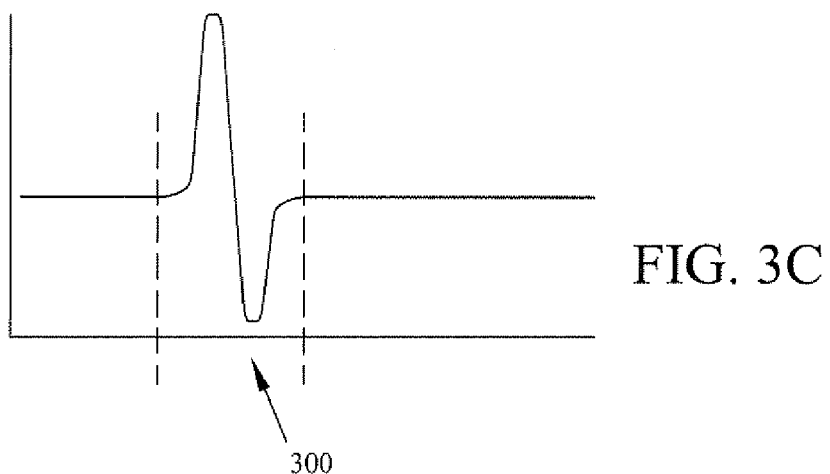

Moreover, the same principles can be extended to samples exhibiting a chemical interaction between the species. FIGS. 3A-3C illustrate the resulting spectrum from a chemical interaction of two spectra. Specifically, FIG. 3A shows the reference Raman spectrum for species P and FIG. 3B shows the image extracted Raman spectrum for species P. If species P chemically interacts with neighboring material, the spectrum resulting from the spectral subtraction of reference P from image extracted P can be expected to have a Raman spectrum revealing a chemical shift as shown in FIG. 3C. Thus, where a sample contains one or more chemically interacting compound species, the Raman peak shift for the compound can be detected as shown in FIGS. 3A-3C.

Figure 4:
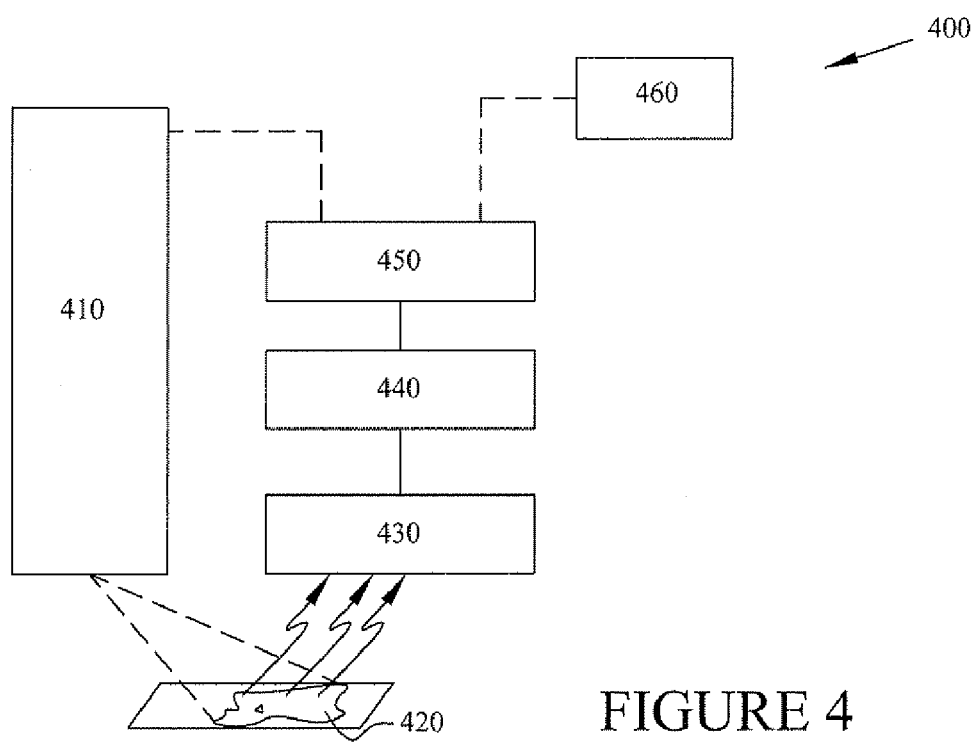
FIG. 4 is a schematic illustration of an exemplary apparatus according to one embodiment of the disclosure.

FIG. 4 is a schematic illustration of an exemplary apparatus according to one embodiment of the disclosure. In FIG. 4, apparatus 400 includes illumination source 410 for providing illumination photons of wavelength $\lambda_{illum}$ to sample 420 to provide interacted photons. Interacted photons 422 may include fluorescence, reflection, transmission, emission and Raman photons. The interacted photons may have a different wavelength depending on the species from which they emanate and the illumination wavelength. In the case where the interacted photons are Raman scattered photons, the wavelength of the interacted photons will reflect the characteristic Raman peak wavelength for that species.

Sample 420 can have a plurality of species (not shown.) Further, the sample can be any biological, organic or inorganic sample suitable for spectral studies. Optical device 430 can receive and direct interacted photons to imaging device 440. The illumination source can be positioned above, near or below the sample. Optical device 430 may include gathering optics, optical train, macro-scope and electro-mechanical devices needed for its operation. Imaging device 440 may include, for example, an optical train for gathering and focusing interacted photons; one or more optical filters for rejecting photons of undesired wavelengths; an LCTF for obtaining spectral images of the sample; and a charge-coupled device for devising a chemical image based on the spectral images of the sample. Imaging device 440 can communicate with peripheral network devices (not shown) such as printers, video recorders or internet communication systems.

Processor 450 communicates with imaging device 440 and can be used to implement the interactive hyperspectral image subtraction steps disclosed above. For example, the processor can be programmed to: (1) identify, for each of the first and second species, an appropriate Raman wavelength; (2) define at least one background wavelength for the frame; (3) identify pixels defined only by the background wavelength; (4) identify pixels defined only by the first species or the second species; (5) identify the remaining pixels, the remaining pixels defined by at least a combination of the first species and the second species; and (6) form a spectral image for either species. These steps can be implemented substantially simultaneously or sequentially. Preferably, the step of identifying the contribution from each of the first and the second species for each of the remaining pixels may also be implemented.

Processor 450 may communicate with operator 460 for interactive subtraction. In addition, the processor may communicate with illumination source 410 in order to increase or decrease illumination wavelength $\lambda_{illum}$ in response to operator 460 request or in response to programmed instructions.

While the principles of the disclosure have been disclosed in relation to specific exemplary embodiments, it is noted that the principles of the invention are not limited thereto and include all modification and variation to the specific embodiments disclosed herein.

What is claimed is:

1. A method of obtaining a spectral image of each of a plurality of predetermined chemical species in a sample, comprising:
   (a) illuminating said sample with a first plurality of photons to produce a second plurality of photons;
   (b) collecting said second plurality of photons and producing a plurality of images of said sample therefrom each of said images comprising a frame consisting essentially of a plurality of pixels;
   (c) for each of said plurality of predetermined chemical species, identifying at least one wavelength range at which said chemical specie exhibits a unique absorption of radiation;
   (d) identifying at least one wavelength range at which none of said plurality of predetermined chemical species exhibits an absorption of radiation;
   (e) in each of said image frames, identifying which of said plurality of pixels do not contain any of said plurality of predetermined chemical species;

(f) in each of said image frames, identifying which of said plurality of pixels contain only a first of said plurality of predetermined chemical species;

(g) repeating said step (f) for each of said plurality of predetermined chemical species;

(h) in each of said image frames, identifying which of said plurality of pixels contain more than one of said plurality of predetermined chemical species;

(i) for each of said plurality of pixels that contains more than one of said plurality of predetermined chemical species, separating the contribution of each of said predetermined chemical species; and (j) composing separate spectral images of each of said plurality of predetermined chemical species in said sample.

2. The method according to claim 1, wherein said wavelength range is in the near IR range.

3. The method according to claim 1, wherein said wavelength range is in the visible range.

4. The method according to claim 1, wherein said wavelength range is in the near UV range.

5. The method according to claim 1, wherein said step (a) comprises illuminating a predetermined area of said sample with substantially monochromatic light.

6. The method according to claim 1, wherein said second plurality of photons are passed through at least one filter.

7. The method according to claim 6, wherein said at least one filter is selected from the group consisting of a tunable filter, a band pass filter, a liquid crystal tunable filter, an interferometer, an acousto optical tunable filter, a dispersive optical device and a computed tomography imaging spectrometer.

8. The method according to claim 1, wherein said spectral image is a spatially accurate wavelength resolved image.

9. The method according to claim 5, wherein said monochromatic light has a wavelength within the range of 500 nm to 800 nm.

10. The method according to claim 9, wherein said monochromatic light is produced using a laser.

11. An apparatus for obtaining a spectral image of each of a plurality of predetermined chemical species in a sample, comprising:

(a) an illumination source for illuminating said sample with a first plurality of photons to form a second plurality of photons;

(b) an optical device for receiving and directing said second plurality of photons to an imaging device;

(c) an imaging device for forming a plurality of images of said sample, each of said images comprising a frame consisting essentially of a plurality of pixels; and (d) a processor in communication with said imaging device, said processor being adapted to:

(i) for each of said plurality of predetermined chemical species, identifying at least one wavelength range at which said chemical specie exhibits a unique absorption of radiation;

(ii) identifying at least one wavelength range at which none of said plurality of predetermined chemical species exhibits an absorption of radiation;

(iii) in each of said image frames, identifying which of said plurality of pixels do not contain any of said plurality of predetermined chemical species;

(iv) in each of said image frames, identifying which of said plurality of pixels contain only a first of said plurality of predetermined chemical species;

(v) repeating said step (iv) for each of said plurality of predetermined chemical species;

(vi) in each of said image frames, identifying which of said plurality of pixels contain more than one of said plurality of predetermined chemical species;

(vii) for each of said plurality of pixels that contains more than one of said plurality of predetermined chemical species, separating the contribution of each of said predetermined chemical species; and (viii) composing separate spectral images of each of said plurality of predetermined chemical species in said sample.

12. The apparatus according to claim 11, wherein said wavelength range is in the near IR range.

13. The apparatus according to claim 11, wherein said wavelength range is in the visible range.

14. The apparatus according to claim 11, wherein said wavelength range is in the near UV range.

15. The apparatus according to claim 11, wherein said illumination source produces substantially monochromatic light.

16. The apparatus according to claim 11, wherein said optical device comprises at least one filter.

17. The apparatus according to claim 16, wherein said at least one filter is selected from the group consisting of a tunable filter, a band pass filter, a liquid crystal tunable filter, an interferometer, an acousto optical tunable filter, a dispersive optical device and a computed tomography imaging spectrometer.

18. The apparatus according to claim 11, wherein said spectral image is a spatially accurate wavelength resolved image.

19. The apparatus according to claim 15, wherein said monochromatic light has a wavelength within the range of 500 nm to 800 nm.

20. The apparatus according to claim 19, wherein said illumination source is a laser.

* * * * *